United States Patent [19]

Domeier et al.

[11] Patent Number: 4,691,025

[45] Date of Patent: Sep. 1, 1987

[54] BISMALEIMIDES AND PREPREG RESINS THEREFROM

[75] Inventors: Linda A. Domeier; Hugh C. Gardner, both of Somerville, N.J.

[73] Assignee: Amoco Corporation, Chicago, Ill.

[21] Appl. No.: 564,400

[22] Filed: Dec. 22, 1983

[51] Int. Cl.[4] ............................................. C08G 20/32
[52] U.S. Cl. .................... 548/521; 528/172; 428/251; 524/726
[58] Field of Search ....................... 548/521; 528/172; 426/251; 524/726

[56] References Cited

U.S. PATENT DOCUMENTS 3,839,289 10/1974 Kwiatkowski et al. ............ 525/451

Primary Examiner—John Kight
Assistant Examiner—M. L. Moore
Attorney, Agent, or Firm—Richard J. Schlott; William H. Magidson; Ralph C. Medhurst

[57] ABSTRACT

Described herein are novel bismaleimides and prepregable resin compositions comprising these bismaleimides and one or more liquid coreactants and optionally, one or more other additives.

9 Claims, No Drawings

BISMALEIMIDES AND PREPREG RESINS THEREFROM

BACKGROUND OF THE INVENTION

Advanced composites are high strength, high modulus materials which are finding increasing use as struc-

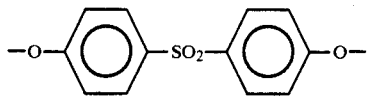

or oligomeric versions such as

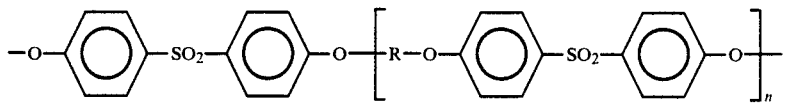

tural components in aircraft, automotive, and sporting goods applications. Typically they comprise structural fibers such as carbon fibers in the form of woven cloth or continuous filaments embedded in a thermosetting resin matrix.

Most advanced composites are fabricated from prepreg, a ready-to-mold sheet of reinforcement impregnated with uncured or partially cured resin. Resin systems containing an epoxide resin and aromatic amine hardener are often used in prepreg since they possess the balance of properties required for this composite fabrication process. State-of-the-art epoxy/carbon fiber composites have high compressive strengths, good fatigue characteristics, and low shrinkage during cure. However, most epoxy formulations absorb moisture which reduces their high temperature properties. As a result they are not suitable for use at 350° F. or greater in a moisture saturated condition. There is therefore a need for resin systems which afford composites which can retain a high level of properties at 350° F. under such moisture saturated conditions.

Most prepreg resins designed for use at 350° F. are made by combining bismaleimides of Formula I with liquid coreactants containing other reactive groups such as amines, epoxides, cyanates or comonomers containing —CH=CH₂, >CH=CH₂, or —CH=CH— groups which can react or polymerize with the carbon-carbon double bonds of the maleimide groups.

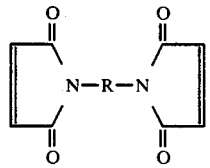

I.

In common bismaleimides, R is the residue of an aromatic diamine such as methylene dianiline or m-phenylene diamine. However, neither of these aromatic bismaleimides has adequate solubility in typical liquid coreactants to be useful in a prepreg resin formulation. Previous modifications to improve the processability of such aromatic bismaleimides have included the use of lower melting, more soluble blends of one or more aromatic bismaleimides with aliphatic bismaleimides. The solubility of aromatic bismaleimides has also been improved by the use of various diamines to extend such bismaleimides in a Michael addition reaction to give a mixture of bismaleimides.

The aromatic bismaleimide of formula I, wherein R has the formula wherein R is the residuum of a dihydric phenol, have also been disclosed and are described in U.S. Pat. No. 3,839,287. A disadvantage of these bismaleimides, however, is again their poor solubility in a various liquid coreactants.

There is a need, therefore, for aromatic bismaleimides with improved solubility with liquid coreactants which can be used in heat resistant resin formulations for structural composites.

THE INVENTION

This invention is directed to:
(i) bismaleimides of formula (II),

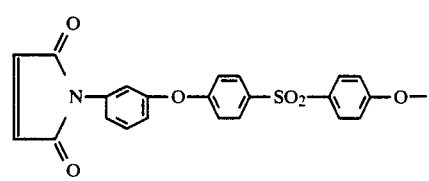

II

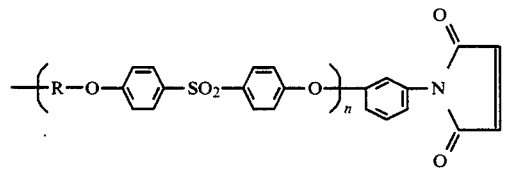

wherein n is 0 to 4, preferably 0 to 2, and R is the residuum of a dihydric phenol, such as resorcinol, bisphenol A, hydroquinone, 4,4'-dihydroxydiphenyl sulfone, 4,4'-dihydroxy-3,3',5,5'-tetramethyldiphenyl sulfone, 4,4'-dihydroxybenzophenone, 3,3',5,5'-tetramethylbisphenol A, 3,4'-dihydroxybenzophenone, 4,4'-biphenol, chlorohydroquinone, methylhydroquinone and the like; and (ii) prepregable resin compositions comprising II and one or more liquid coreactants and optionally, other additives.

These compositions may optionally contain a structural fiber.

In the general formula II, it is also meant to include compositions wherein up to 20% of the maleimide groups have been replaced by other terminal imide groups such as

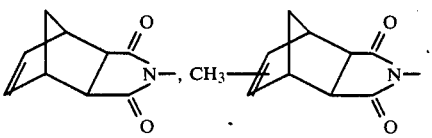

succinimide, phthalimide, and substituted maleimide, succinide, or phthalimide groups.

The bismaleimides of this invention contain maleimide groups which are meta to the connecting ether groups. These have been found to be substantially more soluble and lower melting than those previously described which contains para maliemide groups. Small amounts of the para-para bismaleimide isomer may be added as a modifier to the maleimide of the present invention, however.

The preferred bismaleimides are selected from the following:

replaced by the appropriate anhydride such as nadic anhydride and others.

For example, bismaleimide III is made as shown by the following:

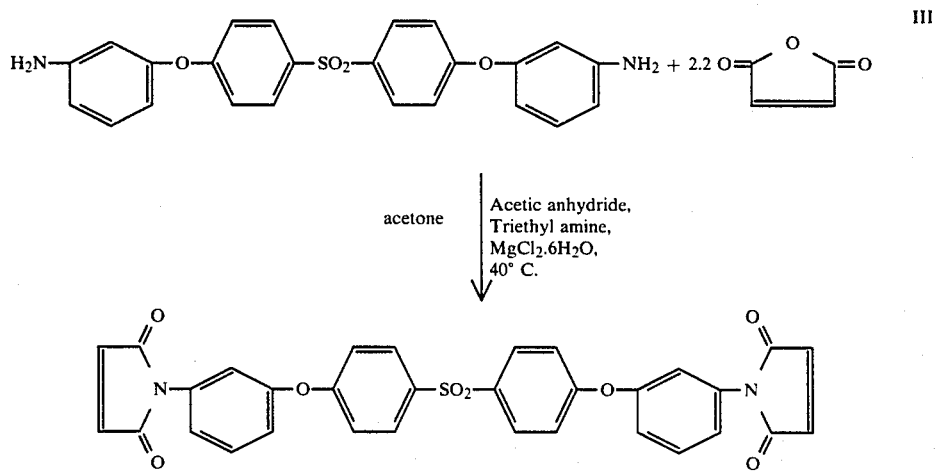

III

The diamines of this invention may be prepared by condensing an aminophenol, a dihalobenzenoid compound and optionally an aromatic diphenol at elevated temperatures in the presence of base in a dipolar aprotic solvent. Preferred aminophenols include m-aminophenol and also alkyl substituted aminophenols. Useful dihalobenzenoid compounds include 4,4'-dichlorodiphenyl sulfone, 4,4'-difluorobenzophenone,

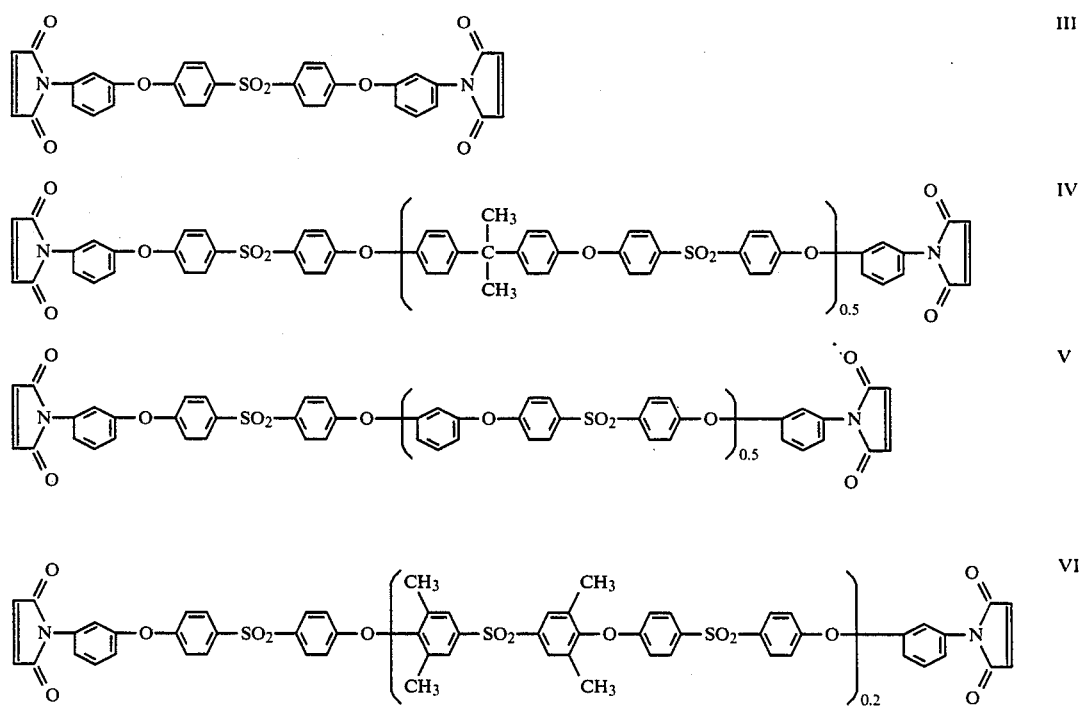

The molecular weight of these bismaleimides is typically about 300 to 2,000 and is preferably about 500 to 1,700. The bismaleimides of this invention are made by condensing aromatic diamines with malic anhydride under dehydrating conditions. In the case of compounds containing up to 20% of other terminal imide groups, a portion of the maleic anhydride would be 4,4'-dichlorobenzophenone, 2,6-dichlorobenzonitrile, 1,2,4,5-tetrachlorobenzene, hexachlorobenzene, and the like. Suitable aromatic diphenols include bisphenol A, hydroquinone, resorcinol, 4,4'-biphenol, 4,4'-dihydroxydiphenyl sulfone, 4,4'-dihydroxydiphenyl sulfide, chlorohydroquinone, methylhydroquinone, 4,4'-dihydroxybenzophenone, 4,4'-dihydroxy-3,3', 5,5'-tetramethyldiphenyl sulfone, and the like. The above compounds may contain one or more alkyl substituents in the aromatic rings. Bases which may be used include sodium hydroxide, potassium hydroxide, sodium carbonate, potassium carbonate, cesium carbonate, sodium bicarbonate, and the like. Dimethyl sulfoxide, N,N-dimethyl acetamide, N-methyl pyrrolidinone, sulfolane and dimethyl sulfone are suitable solvents. An azeotropic solvent such as toluene or chlorobenzene is preferably added to the mixture to assist in removal of water from the reaction mixture.

The preparation of the diamines of this invention may be carried out as described in U.S. Pat. No. 3,895,064. Alternatively the process conditions in British Pat. No. 1,492,366 may be used. Reaction times are typically 8 to 30 hours at temperatures of 140° to 170° C.

The diamines may be prepared by a one-step process in which the aminophenol, dihalobenzenoid compound, optional aromatic diphenol, and base are charged simultaneously to the reactor. Alternatively, a two step process may be used, in which the aminophenol, optional diphenol and base are reacted initially to form phenoxide salts, prior to addition of the dihalobenzenoid compound.

Processes for forming the bismaleimides from the diamines are well known in the art and are described in, for example, U.S. Pat. Nos. 3,839,287; 3,018,290; 4,376,206; 4,154,737; and 4,130,564.

The liquid coreactants in composition (ii) of this invention include N-vinyl-2-pyrrolidinone, ethylene glycol dimethacrylate, diethylene glycol dimethacrylate, trimethylolpropane triacrylate, trimethylolpropane trimethacrylate, pentaerythritol triacrylate, pentaerythritol tetraacrylate, pentaerythritol tetramethacrylate, triallyl isocyanurate, diallyl phthalate, triallyl trimellitate, divinyl benzene, dicylcopentadienyl acrylate, dicyclopentadienyl oxyethyl acrylate, vinylcyclohexene monoepoxide, 1,4-butanediol divinyl ether, 1,4-dihydroxy-2-butene, styrene, alpha methyl styrene, chlorostyrene, p-phenylstyrene, t-butylstyrene, phenyl vinyl ether, unsaturated polyesters, vinyl ester resins, and the like. These comonomers are characterized by the presence of one or more —CH=CH$_2$, >C=CH$_2$, or —C=CH— groups polymerize with the maleimide groups of the bismaleimide.

Other liquid coreactants include epoxy resins which contain one or more epoxy groups having the following formula:

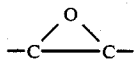

The epoxy groups can be terminal epoxy groups or internal epoxy groups. The epoxides are of two general types: polyglycidyl compounds or products derived from epoxidation of dienes or polyenes. Polyglycidyl compounds contain a plurality of 1,2-epoxide groups derived from the reaction of a polyfunctional active hydrogen containing compound with an excess of an epihalohydrin under basic conditions. When the active hydrogen compound is a polyhydric alcohol or phenol, the resulting epoxide resin contains glycidyl ether groups. A preferred group of polyglycidyl compounds are made via condensation reactions with 2,2-bis(4-hydroxyphenyl)propane, also known as bisphenol A, and have structures such as VII.

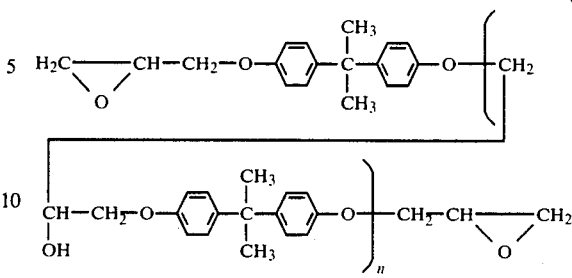

where n has a value from about 0 to about 15. These epoxides are bisphenol-A epoxy resins. They are available commercially under the trade names such as "Epon 828," "Epon 1001", and "Epon 1009" from Shell Chemical Co., and as "DER 331", and "DER 334" from Dow Chemical Co. The most preferred bisphenol A epoxy resins have an "n" value between 0 and 10.

Polyepoxides which are polyglycidyl ethers of 4,4'-dihydroxydiphenyl methane, 4,4'-dihydroxydiphenyl sulfone, 4,4'-biphenol, 4,4'-dihydroxydiphenyl sulfide, phenolphthalein, resorcinol, 4,2'-biphenol, or tris(4-hydroxyphenyl) methane and the like, are useful in this invention. In addition, EPON 1031 (a tetraglycidyl derivative of 1,1,2,2-tetrakis(hydroxyphenyl)ethane from Shell Chemical Company), and Apogen 101, (a methylolated bisphenol A resin from Schaefer Chemical Co.) may also be used. Halogenated polyglycidyl compounds such as D.E.R. 580 (a brominated bisphenol A epoxy resin from Dow Chemical Company) are also useful. Other suitable epoxy resins include polyepoxides prepared from polyols such as pentaerythritol, glycerol, butanediol or trimethylolpropane and an epihalohydrin.

Polyglycidyl derivatives of phenol-formaldehyde novolaks such as VIII where n =0.1 to 8 and cresol-formaldehyde novolaks such as IX where n =0.1 to 8 are also usable.

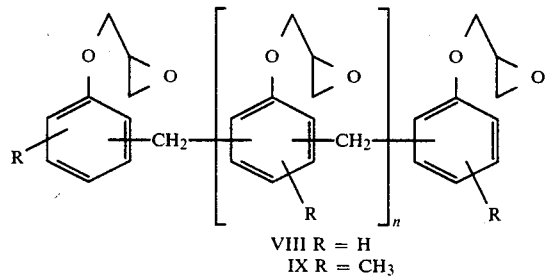

VIII R = H
IX R = CH$_3$

The former are commercially available as D.E.N 431, D.E.N. 438, and D.E.N. 485 from Dow Chemical Company. The latter are available as, for example, ECN 1235, ECN 1273, and ECN 1299 (obtained from Ciba-Geigy Corporation, Ardsley, N.Y.). Other epoxidized novolaks such as SU-8 (obtained from Celanese Polymer Specialties Company, Louisville, K.Y.) are also suitable.

Other polyfunctional active hydrogen compounds besides phenols and alcohols may be used to prepare the polyglycidyl adducts of this invention. They include amines, aminoalcohols and polycarboxylic acids.

Adducts derived from amines include N,N-diglycidyl aniline, N,N-diglycidyl toluidine, N,N,N',N'-tetraglycidylxylylene diamine, (i.e., X) N,N,N',N'-tetraglycidyl-bis (methylamino) cyclohexane (i.e. XI), N,N,N',N'-tetraglycidyl-4,4'-diaminodiphenyl methane, (i.e. XII) N,N,N',N'-tetraglycidyl-3,3'-diaminodiphenyl sulfone, and N,N'-dimethyl-N,N'-diglycidyl-4,4'-diaminodiphenyl methanes. Commerically available resins of this type include Glyamine 135 and Glyamine 125 (obtained from F.I.C. Corporation, San Francisco, CA.), Araldite MY-720 (obtained from Ciba Geigy Corporation) and PGA-X and PGA-C (obtained from The Sherwin-Williams Co., Chicago, Ill.

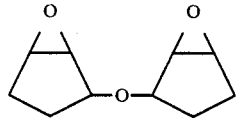
XIII

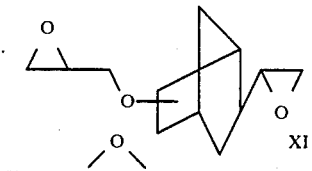
XIV

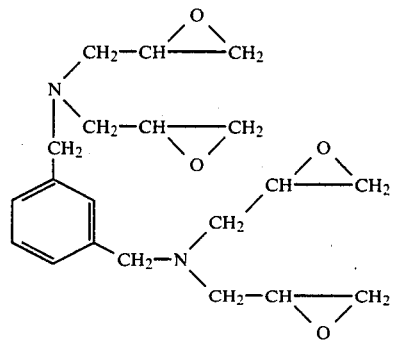
X

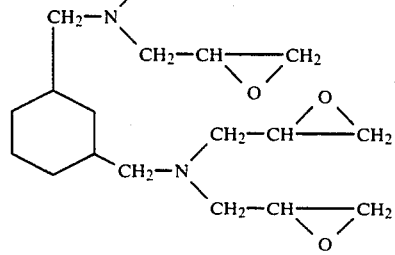
XI

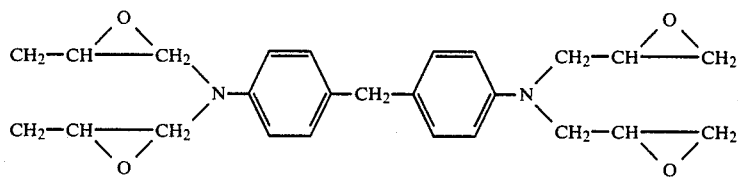
XII

Suitable polyglycidyl adducts derived from amino alcohols include O,N,N-triglycidyl-4-aminophenol, available as Araldite 0500 or Araldite 0510 (obtained from Ciba Geigy Corporation) and O,N,N-triglycidyl-3-aminophenol (available as Glyamine 115 from F.I.C. Corporation).

Also suitable for use herein are the glycidyl esters of carboxylic acids. Such glycidyl esters include, for example, diglycidyl phthalate, diglycidyl terephthalate, diglycidyl isophthalate, and diglycidyl adipate. There may also be used polyepoxides such as triglycidyl cyanurates and isocyanurates, N,N-diglycidyl oxamides, N,N'-diglycidyl derivatives of hydrantoins such as "XB 2793" (obtained from Ciba Geigy Corporation), diglycidyl esters of cycloaliphatic dicarboxylic acids, and polyglycidyl thioethers of polythiols.

Other epoxy-containing materials are copolymers of acrylic acid esters of glycidol such as glycidyl acrylate and glycidyl methacrylate with one or more copolymerizable vinyl compounds. Examples of such copolymers are 1:1 styrene-glycidyl methacrylate, 1:1 methyl methacrylate-glycidyl acrylate and 62.5:24:13.5 methyl methacrylate:ethyl acrylate:glycidyl methacrylate.

Silicone resins containing epoxy functionality, e.g., 2,4,6,8,10-pentakis [3-(2,3-epoxypropoxy)propyl]-2,4,6,8,10-pentamethylcyclopentasiloxane and the diglycidyl ether of 1,3-bis-(3-hydroxypropyl)tetramethyldisiloxane) are also usable.

The second group of epoxy resins is prepared by epoxidation of dienes or polyenes. Resins of this type include bis(2,3epoxycyclopentyl) ether, XIII, reaction products of XIII with ethylene glycol which are described in U.S. Patent 3,398,102, 5(6)-glycidyl-2-(1,2-epoxyethyl)bicyclo[2.2.1]heptane, XIV, and dicyclopentadiene diepoxide. Commercial examples of these epoxides include vinylcyclohexene dioxide, e.g., "ERL-4206" (obtained from Union Carbide Corp.), 3,4-epoxycyclohexylmethyl 3,4-epoxycyclohexane carboxylate, e.g., "ERL-4221" (obtained from Union Carbide Corp.), 3,4-epoxy-6-methylcyclohexylmethyl 3,4-epoxy-6-methylcyclohexane carboxylate, e.g., "ERL-4201" (obtained from Union Carbide Corp.), bis(3,4-epoxy-6-methylcyclohexylmethyl) adipate, e.g., "ERL-4289" (obtained from Union Carbide Corp.), dipentene dioxide, e.g., "ERL-4269" (obtained from Union Carbide Corp.) 2-(3,4-epoxycyclohexyl-5,5-spiro-3,4-epoxy)cyclohexanemetadioxane, e.g., "ERL-4234" (obtained from Union Carbide Corp.) and epoxidized polybutadiene, e.g., "Oxiron 2001" (obtained from FMC Corp.)

Other suitable cycloaliphatic epoxides include those described in U.S. Pat. Nos. 2,750,395; 2,890,194; and 3,318,822 which are incorporated herein by reference, and the following:

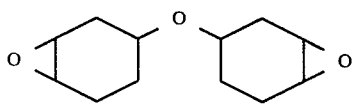

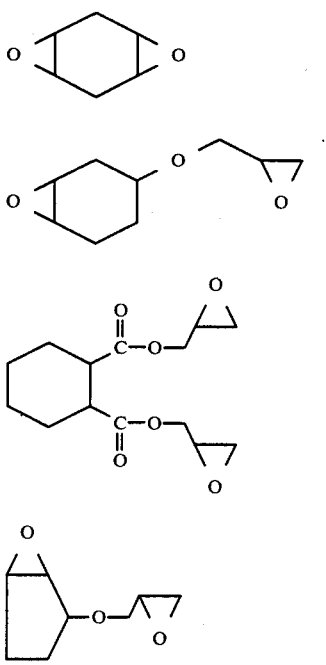

Other suitable epoxides include:

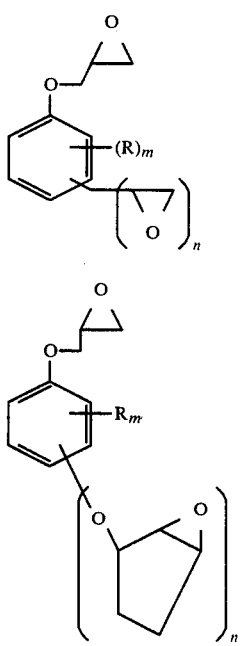

where n is 1 to 4, m is (5-n), and R is H, halogen or $C_1$ to $C_4$ alkyl.

The preferred epoxy resins are bis(2,3-epoxycyclopentyl)ether, adducts of this ether with ethylene glycol which are described in U.S. Pat. No. 3,398,102, N,N,N',N'-tetraglycidyl xylylenediamine, N,N,N',N'-tetraglycidyl methylene dianiline, O,N,N-triglycidyl-4-aminophenol, and O,N,N-triglycidyl-3-aminophenol.

If epoxy resins are used, it is desirable to add an aromatic diamine to the formulation. The diamine should have a low level of reactivity with epoxy resin and the bismaleimide at room temperature. Suitable diamines include 4,4'-diaminodiphenyl sulfone, 3,3'-diaminodiphenyl sulfone, 3,4'-diaminobenzophenone, 4,4'-diaminobenzophenone, 4,4'-bis(3-aminophenoxy)-diphenyl sulfone, and the like. A stoichimetry of 0.1 to 1.0 equivalents of -NH per equivalent of (1,2-epoxide group plus maleimide group) may be used.

Diamines may also be used even if no epoxy is used. In this case the diamines may react during the cure cycle with the bismaleimides. When epoxies are present, the diamines may react with either the epoxy or maleimide groups.

The composition may additionally contain an accelerator to increase the rate of cure of the epoxy plus amine reation. Accelerators which may be used herein include Lewis acids; amine complexes such as $BF_3$.monoethylamine, $BF_3$.piperdine, $BF_3$. 2-methylimidazole; amines, such as imidazole and its derivatives such as 4-ethyl-2-methylimidazole, 1-methylimidazole, 2-methylimidazole; N,N-dimethylbenzylamine; acid salts of tertiary amines, such as the p-toluene sulfonic acid:imidazole complex, salts of trifluoro methane sulfonic acid, such as FC-520 (obtained from 3M Company), organophosphonium halides and dicyandiamide. If used, the accelerator may be from 1 to 6 percent by weight of the epoxy component.

The composition may also contain compounds with one or more cyanate ester groups.

By cyanate ester is meant a compound having at least one cyanate group in its molecule. The cyanate ester is represented by the formula $$R-(P-C\equiv N)_m$$

wherein R is a residue derived from an aromatic hydrocarbon selected from the group consisting of benzene, biphenyl and naphthalene, or a residue derived from a compound in which at least two benzene rings are bonded to each other by a bridging member selected from the group consisting of

wherein $R^1$ and $R^2$ are the same or different and each represents a hydrogen atom or an alkyl group containing 1 to 4 carbon atoms,

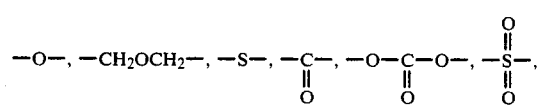

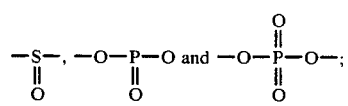

said aromatic nucleus is optionally substituted by a substituent selected from the group consisting of alkyl groups containing 1 to 4 carbon atoms, alkoxy groups containing 1 to 4 carbon atoms, chlorine and bromine; m is an integer of 1 to 5, and the cyanate group is always directly bonded to the aromatic nucleus.

Examples of the cyanate ester include cyanatobenzene, dicyanatobenzene; 1,3,5-tricyanatobenzene; 1,3-, 1,4-, 1,6-, 1,8-, 2,6-or 2,7-dicyanatonaphthalene; 1,3,6- tricyanatonaphthalene; 4,4'-dicyanatobiphenyl; bis(4-cyanatophenyl)methane; 2,2-bis(4-cyanatophenyl)propane, 2,2-bis(3,5-dichloro-4-cyanatophenyl)propane, 2,2-bis(3,5-diblomo-4-dicyanatophenyl)propane; bis(4-cyanatophenyl)ether; bis(4-cyanatophenyl)thioether; bis(4-cyanatophenyl)sulfone; tris(4-cyanatophenyl)phosphite; tris(4-cyanatophenyl)phosphate; bis(3-chloro-4-cyanatophenyl)methane; cyanated novolak derived from novolak cyanated disphenol type polycarbonate oligomer derived from bisphenol type polycarbonate oligomer and mixture thereof.

The above mentioned cyanate esters may be used as mixtures.

Prepolymers may be used containing a sym-triazine ring which is prepared by the trimerization of the cyanate groups of the cyanate ester, and which have an average molecular weight of at least 400 but no more than 6,000. Such prepolymers can be prepared by polymerizing the above cyanate esters in the presence of, as a catalyst, an acid such as a mineral acid or Lewis acid, a base such as sodium hydroxide, a sodium alcoholate or a tertiary amine, or a salt such as sodium carbonate or lithium chloride.

The cyanate ester can be used in the form of a mixture of the monomer and the prepolymer.

The compositions of this invention may optionally contain a thermoplastic polymer. These materials have beneficial effects on the viscosity and film strength characteristics of the bismaleimide/liquid coreactant mixture.

The thermoplastic polymers used in this invention include polyarylethers of formula XV which are described in U.S. Pat. Nos. 4,108,837 and 4,175,175,

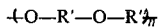   XV wherein R' is a residuum of a dihydric phenol such as bisphenol A, hydroquinone, resorcinol, 4,4-biphenol, 4,4'-dihydroxydiphenyl sulfone, 4,4'-dihydroxy-3,3' 5,5'-tetramethyldiphenyl sulfide, 4,4'-dihydroxy-3',3',5,5-tetramethyldiphenyl sulfone and the like. R" is a residuum of a benzenoid compound susceptible to nucleophilic aromatic substitution reactions such as 4,4'-dichlorodiphenyl sulfone, 4,4'-difluorobenzophenone, and the like. The average value of n is from about 8 to about 120.

Other suitable polyarylethers are described in U.S. Pat. No. 3,332,209.

Also suitable are polyhydroxyethers of the formula:

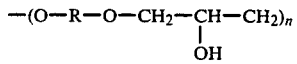   XV where R has the same meaning as for Formula VII and the average value of n is between about 8 and about 300; and polycarbonates such as those based on bisphenol A, tetramethyl bisphenol A, 4,4'-dihydroxydiphenyl sulfone, 4,4'-dihydroxy-3,3', 5,5'-tetramethyl- diphenyl sulfone, hydroquinone, resorcinol, 4,4'-dihydroxy-3,3', 5,5'-tetramethyl diphenyl sulfide, 4,4'biphenol, 4,4'-dihydroxydiphenyl sulfide, phenolphthalein, 2,2,4,4-tetramethyl-1,3-cyclobutane diol, and the like. Other suitable thermoplastics include poly (ε-caprolactone); polybutadiene; polybutadiene/acrylonitrile copolymers, including those optionally containing amine, carboxyl, hydroxy, or —SH groups; polyesters, such as poly(butylene terephthalate); poly(ethylene terephthalate); polyetherimides such as the Ultem resins (obtained from the General Electric Company); acrylonitrile/ butadiene/styrene copolymers, polyamides such as nylon 6, nylon 6,6, nylon 6,12, and Trogamid T (obtained from Dynamit Nobel Corporation); poly(amide imides) such as Torlon poly(amide imide) (obtained from Amoco Chemical Corporation, Napierville, Ill.); polyolefins, polyethylene oxide; poly(butyl methacrylate); impact-modified polystyrene; sulfonated polyethylene; polyarylates such as those derived from bisphenol A and isophthalic and terephthalic acid; poly(2,6- dimethyl phenylene oxide); polyvinyl chloride and its copolymers; polyacetals; polyphenylene sulfide and the like.

Poly(vinyl acetate) and copolymers of vinyl acetate with other vinyl and acrylic monomers may also be used. Thermoplastics such as low profile additives, for example, LP-40A, may also be used.

Also suitable are vinyl methyl or vinyl phenyl silicone rubbers such as polymers of the formula —R$_2$Si-O—wherein up to 10% of the R groups are vinyl, the remainder being either methyl and/or phenyl.

The preferred thermoplastics include polysulfones, phenoxy resins, and polyarylates.

The structural fibers which are useful in this invention include carbon, graphite, glass, silicon carbide, poly(benzothiazole), poly(benzimidazole), poly(benzoxazole), aluminum, titanium, boron, and aromatic polyamide fibers. These fibers are characterized by a tensile strength of greater than 100,000 psi, a tensile modulus of greater than two million psi, and a decomposition temperature of greater than 200° C. The fibers may be used in the form of continuous tows (1000 to 400,000 filaments each), woven cloth, whiskers, chopped fiber or random mat. The preferred fibers are carbon fibers, aromatic polyamide fibers, such as Kevlar 49 fiber (obtained from E. I. duPont de Nemours, Inc., Wilmington, Del.), and silicon carbide fibers.

The compositions of component ii contains 1 to 99 weight percent, preferably 20-98 percent of the bismaleimide; 1 to about 60 percent, preferably 3 to 40 percent of the liquid coreactant or mixture of coreactants comprising molecules with one or more amino, epoxy, cyanate, and/or vinyl groups such as —CH=CH$_2$, >C=CH$_2$, or —CH=CH—; and 1 to about 40 percent, preferably 2 to 30 percent of other additives such as thermoplastic polymers and other solid coreactants.

Additional components in the composition include initators for vinyl polymerization such as di-t-butyl peroxide, dicumyl peroxide, 1,1-bis-(t-butylperoxy)cyclohexane, azo-bis(isobutyronitrile), t-butyl perbenzoate, and the like. The initiator comprises from 0 to 3 percent by weight of the total composition.

Inhibitors for vinyl polymerizations may also be used. They include hydroquinone, t-butyl hydroquinone, benzoquinone, p-methoxyphenol, and 4-nitro-m-cresol. Inhibitors are present in amounts of from 0 to 2 percent by weight of the total composition.

When a structural fiber is used, the amount of fiber in the total composition is between about 10 and about 90 percent by weight, preferably between about 20 to about 85 percent by weight.

Preimpregnated reinforcement may be made from the compositions of this invention by combining component ii with a structural fiber.

Preimpregnated reinforcement may be prepared by several techniques known in the art, such as wet winding or hot melt. In one method of making impregnated tow or undirectional tape, the fiber is passed into a bath of the resin mixture. A non-reactive, volatile solvent such as methyl ethyl ketone may be optionally included in the resin bath to reduce viscosity. After impregnation, the reinforcement is passed through a die to remove excess resin, sandwiched between plies of release paper, passed through a set of heated rollers, cooled, and taken up on a spool. It is used within a few days or may be stored for months at 0° F.

Composites may be prepared by curing the preimpregnated reinforcement using heat and optionally pressure. Vacuum bag/autoclave cures work well with these compositions. Laminates may also be prepared via wet layup followed by compression molding, resin transfer molding, or by resin injection, as described in European Patent Application No. 0019149 published Nov. 26, 1980. Typical cure temperatures are 100° F. to 600° F., preferably 180° F. to 490° F.

The compositions of this invention may also be used for filament winding. In this composite fabrication process, continuous reinforcement in the form of tape or tow—either previously impregnated with resin or impregnated during winding—is placed over a rotating and removable form or mandrel in a previously determined pattern. Generally the shape is a surface of revolution and contains end closures. When the proper number of layers are applied, the wound form is cured in an oven or autoclave and the mandrel removed.

Tacky drapable prepreg can be obtained with a wide variety of compositions. Long prepreg shelf lives can be obtained-typically one to four weeks.

The compositions of this invention may be used as matrix resins for composites, high temperature coatings, and adhesives. When reinforced with structural fibers, they may be used as aircraft parts such as wing skins, wing-to-body fairings, floor panels, flaps, radomes; as automotive parts such as driveshafts, bumpers, and springs; and as pressure vessels, tanks and pipes. They are also suitable for protective armor on military vehicles and sporting goods applications such as golf shafts, tennis rackets, and fishing rods.

In addition to structural fibers, the composition may also contain particulate fillers such as talc, mica, calcium carbonate, aluminum trihydrate, glass microballoons, phenolic thermospheres, and carbon black. Up to half of the weight structural fiber in the composition may be replaced by filler. Thixotropic agents such as fumed silica may also be used.

EXAMPLES

The following examples serve to give specific illustrations of the practice of this invention but they are not intended in any way to limit the scope of this invention.

EXAMPLE 1

Preparation of the Bismaleimide of Formula III

A two liter round bottom flask equipped with a paddle stirrer, condenser, nitrogen inlet and bubbler, thermometer, heating mantle, and Therm-o-Watch controller was charged with 240 ml acetone and 64.8 g. maleic anhydride. To the stirring mixture was added a solution of 129.6 g. of 4,4'-bis(3-aminophenoxy)diphenyl sulfone in 240 ml acetone in portions over 30 minutes. The exotherm was controlled at about 40° C. by lowering the heating mantle as needed. The reaction mixture was maintained at 40° C. for an additional 30 minutes after addition was complete during which time it turned into an opaque slurry. To this mixture was added 3.26 g of magnesium chloride hexahydrate ($MgCl_2.H_2O$), and 16 ml of triethylamine. A 164 g charge of acetic anhydride was then gradually added over 15 minutes while controlling the reaction temperature at about 40° C. The reaction was then maintained at 40° C. for about 20 hours. [Note: the reaction was complete after about 5 hours by liquid chromatographic analysis.]

The mixture was then diluted with 960 ml of dichloromethane, transferred to a 12 l. separatory flask, washed five times with one liter portions of aqueous 0.25 molar potassium carbonate and then washed once with one liter of very dilute brine. The organic solution was then added to ten parts isopropanol in a rapidly stirring blender. The precipitated solid was collected by filtration and washed once with isopropanol. After drying under vacuum at 55° C, the yield of bismaleimide was 146 g. or 80%. The material had a melting point of 90°-100° C. and the NMR, IR, and mass spectrum were consistent with the expected bismaleimide (BMI):

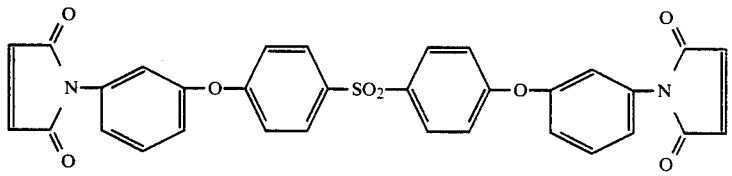

EXAMPLE 2

Preparation of the Bismaleimide of Formula IV

A five liter flask equipped with a paddle stirrer, condenser, nitrogen inlet and bubbler, thermometer, electric heating mantle, and Therm-o-Watch controller was charged with 300 ml of acetone and 98.06 g of maleic anhydride. To the stirred solution was added a solution of 332 g of an oligomeric diamine with an Mn of 652 in 500 ml of acetone over 30 minutes. [The oligomeric diamine was prepared by reacting dichlorodiphenylsulfone, bisphenol A, and the sodium salt of m-aminophenol.]The reaction mixture was heated to 35° C. and held there for about 2 hours. Then it was charged with 4.07 g of magnesium chloride hexahydrate ($MgC_2.6H_2O$) and 20 ml of triethylamine, followed by 204 g of acetic anhydride, which was added over about 15 minutes. The reaction mixture was maintained at 40° C. for 4 hours and then stirred at room temperature for about 18 hours. After the reaction mixture was diluted with 750 ml additional acetone, it was added to about ten parts of water in a rapidly stirring blender. The precipitated product was collected by filtration and washed 5 times with 2 l. of water. After drying, the product had a melting point of about 121°-123° C. A total of 378 g (93%) of product were obtained. The proton NMR spectrum was consistent with the expected bismaleimide product

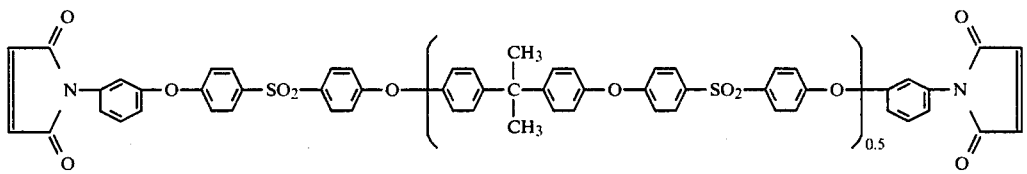

EXAMPLE 3

Preparation of Bismaleimide/Coreactant Casting

A mixture of 7.5g of the bismaleimide (BMI) prepared in Example 1 (ground to 30 mesh) and 3 ml of N-vinyl-2-pyrrolidinone (NVP) containing about 1,000 ppm of p-methoxyphenol was placed in a 25 ml round bottom flask attached to a rotary evaporator. The mixture was rotated and heated in an oil bath at 80° C. while being subjected to a vacuum of about 10 mm of mercury. After about 10 minutes, the clear solution was poured into a small casting frame.

The coating was cured by heating from 35° C to 100° C. at 0.25° C./min. holding at 100° C. for 1 hr. heating from 100° C. to 179° C. at 0.25° C./min, holding at 179° C. for 3 hours, and then cooling to room temperature. Other cure schedules could also be used having shorter or longer hold periods at 179° C. Rectangular samples were cut from the casting and tested by dynamic mechanical analysis using a heating rate of 5° C./min.

The cured material had a glass transition temperature (Tg) of 211° C. The casting was transparent and dark red. The uncured material was also transparent at room temperature and remained a very viscous liquid for over four weeks.

The para-para isomer of the bismaleimide was not soluble in 3 ml of NVP and the formulation could not be cast. This isomer was similarly insoluble or only partially soluble in the coreactant mixtures of the following examples.

EXAMPLE 4

Preparation of Bismaleimide/Coreactant Casting

The procedure of Example 3 was repeated except that 7.5 g of BMI and 2 ml of NVP were used. The Tg of the cured material was 230° C. The uncured material remained tacky for over 4 weeks.

EXAMPLE 5

Preparation of Bismaleimide/Coreactant Casting

The procedure of Example 3 was repeated except that 7.5 g of BMI, 1 ml of NVP, and 1 ml of trimethylolpropane triacrylate were used. The Tg of the cured material was 199° C. Portions of this casting were post-cured for 2.5 hours at 240° C. The Tg of the post-cured material was 287° C. The uncured material was homogeneous and tacky at room temperature.

EXAMPLE 6

Preparation of Bismaleimide/Coreactant Casting

The procedure of Example 3 was repeated except that 7.5 g of BMI and 2 ml of 1-vinyl-3,4-epoxycyclohexane were used. The cured material gave a hard casting. The uncured material was clear and tacky at room temperature.

EXAMPLE 7

Preparation of Bismaleimide/Coreactant Casting

The procedure of Example 3 was repeated except that 7.5 g of BMI, 3 ml of NVP, and 1 g of 4,4'-diaminodiphenyl sulfone were used. The cured material gave a hard casting. The uncured material was clear and tacky at room temperature.

EXAMPLE 8

Preparation of Bismaleimide/Coreactant Casting

The procedure of Example 3 was repeated except that 7.5 g of BMI, 1 g of 4,4'-diaminodiphenyl sulfone, and 2 g of N,N,N',N'-tetraglycidyl-4,4'-diaminodiphenyl methane (available from Ciba-Geigy Corporation) were used. The cured material gave a hard casting. The uncured material was clear and tacky at room temperature.

EXAMPLE 9

Preparation of Bismaleimide/Coreactant Casting

The procedure of Example 3 was repeated except that 7.5 g of BMI, 2 ml of NVP, and 3 g of a bismaleimide/cyanate ester resin (BT 2160 available from Mitsubishi Gas Chemical Co., Tokyo, Japan) were used. The cyanate ester resin was comprised of the dicyanate ester of bisphenol A and the bismaleimide of 4,4'-diaminodiphenyl methane. The cured material gave a hard casting. The uncured material was clear and tacky at room temperature.

EXAMPLE 10

Preparation of Bismaleimide/Coreactant Casting

The procedure of Example 3 was repeated except that 7.5 g of BMI, 4 ml of NVP, and 2 g of 4,4'-diaminodiphenyl sulfone were used. The cured material gave a hard casting. The uncured material was clear and tacky at room temperature.

EXAMPLE 11

Preparation of Bismaleimide/Coreactant Casting

The procedure of Example 3 was repeated except that 7.5 g of BMI, 2 ml of NVP, 2 g of bis(2,3-epoxycyclopentyl)ether, and 2 g of 4,4'-bis(3-aminophenoxy)-diphenyl sulfone were used. The cured material gave a hard casting. The uncured material was clear and tacky at room temperature.

EXAMPLE 12

Preparation of Bismaleimide/Coreactant Casting

The procedure of Example 3 was repeated except that 7.5 g of BMI, 2 ml of NVP, 2 g of an adduct of bis(2,3-epoxycyclopentyl)ether and ethylene glycol having an epoxide equivalent weight of 130-135, and 2 g of 4,4'-bis(3-aminophenoxy)diphenyl sulfone were used. The cured material gave a hard casting. The uncured material was clear and tacky at room temperature.

EXAMPLE 13

Preparation of Bismaleimide/Coreactant Casting

The procedure of Example 3 was repeated except that 7.5 g of BMI, 4 g of an adduct of bis(2,3-epoxycyclopentyl)ether, and ethylene glycol having an epoxide equivalent weight of 130–135, and 2 g of 4,4'-bis(3-aminophenoxy)diphenyl sulfone were used. The cured material gave a hard casting. The uncured material was clear and tacky at room temperature.

EXAMPLE 14

Preparation of Bismaleimide/Coreactant Casting

The procedure of Example 3 was repeated except that 7.5 g of BMI and 3 ml of NVP containing 5% by weight P-1700 polysulfone and 5% PKHH phenoxy (both thermoplastics available from Union Carbide Corp., Danbury, Conn.) were used. The Tg of the cured material was 217° C. The cured material gave a hard casting. The uncured material was clear and tacky at room temperature.

EXAMPLE 15

Preparation of Bismaleimide/Coreactant Casting

The procedure of Example 3 was repeated except that 7.5 g of BMI, 1 ml of NVP, 1 ml of ethylene glycol dimethacrylate were used. The Tg of the cured material was 230° C. The uncured material was clear and tacky at room temperature.

EXAMPLE 16

Preparation of Bismaleimide/Coreactant Casting

The procedure of Example 3 was repeated except that 7.5 g of BMI and 3 ml of NVP containing 10% by weight PKHH phenoxy resin were used. The Tg of the cured material was 222° C. The uncured material was clear and tacky at room temperature.

EXAMPLE 17

Preparation of Bismaleimide/Coreactant Casting

The procedure of Example 3 was repeated except that 7.0 g of BMI, 2 ml of NVP, and 0.5 g of the bis-maleimide of 4,4'-bis(4-aminophenoxy)diphenyl sulfone were used. The Tg of the cured material was 215° C. The uncured material was clear and tacky at room temperature.

What is claimed is:

1. A bismaleimide of the formula:

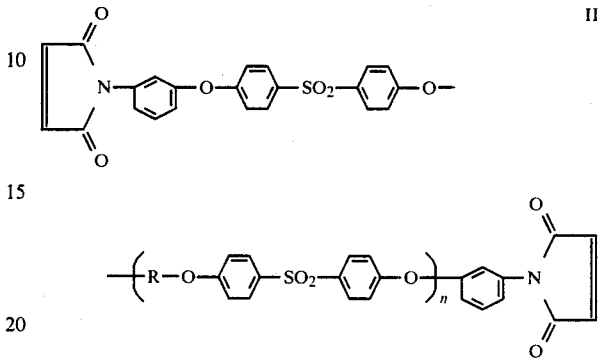

wherein n is 0 to 4 and R is the residuum of a dihydric phenol.

2. A bismaleimide as defined in claim 1 where the dihydric phenol is bis-phenol A.

3. A bismaleimide as defined in claim 1 of the following formula:

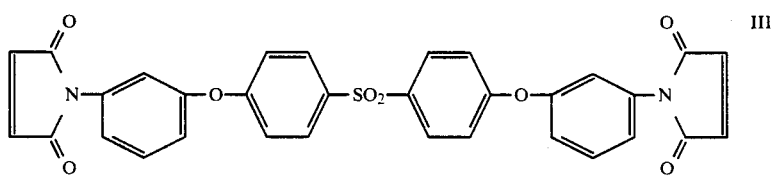

4. A bismaleimide as defined in claim 1 of the following formula:

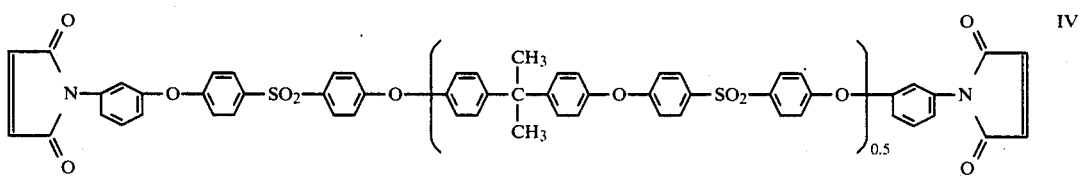

5. In a curable composition comprising:
(a) from 10 to 100 parts by weight of a mixture of from 1 to 99 wt% bismaleimide, from 1 to 60 wt% of at least one coreactant having reactive groups selected from the group consisting of amino, epoxide, cyanate, —CH=CH$_2$, —C=CH$_2$ and —CH=CH—groups, and from 0 to 30 wt% thermoplastic; and
(b) from 0 to 90 parts by weight of a structural fiber; the improvement wherein said bismaleimide is a bis-meta-maleimide compound having the structure:

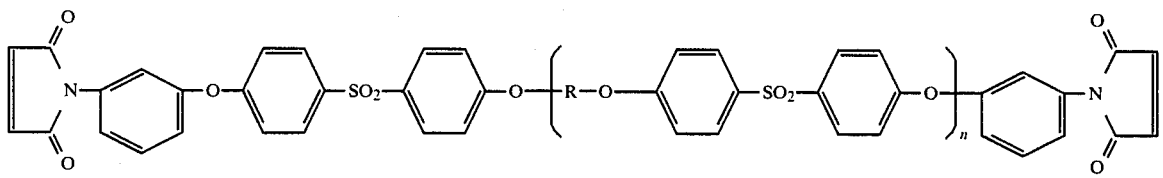
wherein n is 0 to 4, and R is the residuum of a dihydric phenol.
6. The composition of claim 5 wherein said dihydric phenol is bisphenol A.
7. The composition of claim 6 wherein said bis-meta-maleimide compound is a mixture of compounds having an average n=0 to 1.
8. The composition of claim 7 wherein n=0.5.
9. The composition of claim 5 wherein said bis-meta-maleimide is
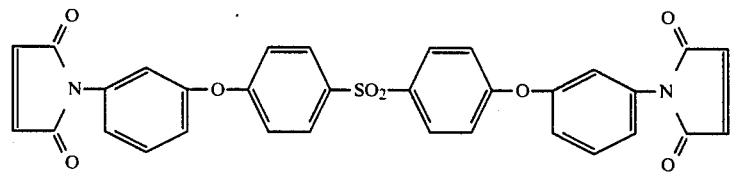
* * * * *